(12) United States Patent
Loessner et al.

(10) Patent No.: US 7,438,901 B2
(45) Date of Patent: Oct. 21, 2008

(54) **VIRULENT PHAGES TO CONTROL *LISTERIA MONOCYTOGENES* IN FOODSTUFFS AND IN FOOD PROCESSING PLANTS**

(75) Inventors: Martin Loessner, Binz (CH); Richard M. Carlton, Port Washington, NY (US)

(73) Assignee: Exponential Biotherapies, Inc., Port Washington, NY (US)

( * ) Notice: Subject to any disclaimer, the term of this patent is extended or adjusted under 35 U.S.C. 154(b) by 258 days.

(21) Appl. No.: 10/516,507

(22) PCT Filed: Jul. 7, 2003

(86) PCT No.: PCT/US03/21061

§ 371 (c)(1),
(2), (4) Date: Dec. 1, 2004

(87) PCT Pub. No.: WO2004/004495

PCT Pub. Date: Jan. 15, 2004

(65) Prior Publication Data

US 2005/0175594 A1      Aug. 11, 2005

Related U.S. Application Data

(60) Provisional application No. 60/393,842, filed on Jul. 8, 2002, provisional application No. 60/393,841, filed on Jul. 8, 2002.

(51) Int. Cl.
*A01N 63/00*     (2006.01)
(52) U.S. Cl. .................................................. 424/93.6
(58) Field of Classification Search ....................... None
See application file for complete search history.

(56) References Cited

U.S. PATENT DOCUMENTS 5,006,347 A * 4/1991 Day et al. .................... 426/36

FOREIGN PATENT DOCUMENTS

DE         43 26 617 C     6/1994
GB         2 253 859 A     9/1992

OTHER PUBLICATIONS

Loessner M.J. & Busse M. "Bacteriophage typing of Listeria species", Applied and Environmental Microbiology, Jun. 1990, 56(6): 1912-1918, entire document.*
Roy et al., "Biological inactivation of adhering *Listeria monocytogenes* by listeriaphages and a quaternary ammonium compound", Applied and Environmental Microbiology, vol. 59, No. 9, 1993, pp. 2914-2917.
Gaeng et al., "Gene cloning and expression and secretion of *Listeria monocytogenes* bacteriophage-lytic enzymes in *Lactococcus lactis*", Applied and Environmental Microbiology, vol. 66, No. 7, Jul. 2000, pp. 2951-2958.
Loessner et al., "Construction of luciferase reporter bacteriophage A511::luxAB for rapid and sensitive detection of viable Listeria cells", Applied and Environmental Microbiology, vol. 62, No. 4, Apr. 1, 1996, pp. 1133-1140.

* cited by examiner

*Primary Examiner*—Irene Marx
*Assistant Examiner*—Satyendra K Singh
(74) *Attorney, Agent, or Firm*—Browdy and Neimark, P.L.L.C.

(57) ABSTRACT

The present invention relates to virulent (lytic) *Listeria monocytogenes* phage from the Myoviridae family, preferably P100, alone or in combination with other virulent phages. P100 and the endolysin from P100 can be administered to food products, to the components that will be added to food products, and/or to the infrastructure of the food processing plants within which such food products are processed, or the containers or wraps in which such foods are stored and/or shipped, in order to reduce *Listeria monocytogenes* contamination. P100 can also be used in the present invention to identify *Listeria monocytogenes* bacteria present on (or within) foodstuffs, as well as those *Listeria monocytogenes* bacteria present in the equipment or the general environment of the food processing plants in which the foodstuffs are being processed and in animals infected with *Listeria monocytogenes*. The phage and the endolysin of the present invention can also be used to treat animals infected with *Listeria monocytogenes*. P100 will kill the bacteria that are within its host range with great efficiency and will propagate to high titer thereon. P100 can be combined with other lytic phage, and/or with other antimicrobial agents to reduce or eliminate *Listeria*.

19 Claims, 3 Drawing Sheets

VIRULENT PHAGES TO CONTROL *LISTERIA MONOCYTOGENES* IN FOODSTUFFS AND IN FOOD PROCESSING PLANTS

CROSS REFERENCE TO RELATED APPLICATION

This application is a 35 USC § 371 National Phase Entry Application from PCT/US03/21061, filed Jul. 7, 2003, and designating the U.S., which claims priority from provisional applications 60/393,842 and 60/393,841, both filed Jul. 8, 2002.

BACKGROUND OF THE INVENTION

1. Field of the Invention

The present invention relates to the use of a particular class of bacteriophages ("phage") known as virulent phages that are lytic for the bacterial species *Listeria monocytogenes*, and which is shown in the present invention to reduce the counts of these bacteria and/or to prevent their growth in the first place, and to be useful for identifying *Listeria monocytogenes*, in foods products (including but not limited to the dairy industry) as well as on processing equipment and other sites in food industry facilities, and as a therapeutic agent for treating animals infected with *Listeria monocytogenes*. One specific example of a virulent *Listeria monocytogenes* phage, is a phage designated P100, recently discovered by one of the present inventors. The present invention also relates to an endolysin produced by P100 and the use of the endolysin for reducing the amount of *Listeria monocytogenes* in foods products as well as on processing equipment and other sites in food industry facilities, and in or on animals infected with *Listeria monocytogenes* and to methods that will enable additional phage that have lytic properties to be developed and/or isolated.

Phages, as antibacterial agents, have the advantage of replicating within the bacterial target. Thus, when their progeny lyse the cell and escape into the extracellular milieu, they can infect and multiply in succeeding generations of bacteria, producing progeny levels far greater than that of the binary growth of the target bacteria, thereby increasing the phage population exponentially in numbers at the expense of the bacterial targets.

The concept of using phages to identify bacterial contamination in food products {and facilities, equipment}, in general, has been described in the scientific literature (see, e.g. Greer, J. Food Prot., 49:104-109, 1986). The concept of using specific *Listeria* phages in particular, to identify *Listeria* contamination of dairy products and facilities/equipment in specific, was described as early as 1990 (Loessner et. al., Applied and Environmental Microbiology, Jun. 1990, p. 1912-1918). The present invention concern the use of a recently discovered *Listeria* phage with specific, essential and relevant properties, which makes it particularly suitable for identifying and controlling *Listeria* contamination of dairy products, facilities and equipment.

In addition to the general scientific literature on the subject, there is also patent literature that teaches the utility of phages in general to control bacterial contaminations in food processing plants and in foodstuffs. See for example U.S. Pat. No. 5,006,347 issued on Apr. 9, 1991, U.S. Pat. No. 4,851,240 issued on Jul. 25, 1989, GB 2 253 859 A published on Sep. 23, 1992 and EP 0414304A2 published on Feb. 27, 1991. However, none of the above discussed patents disclose a *Listeria* phage which was actually tested and shown to successfully control bacterial contamination in food processing plants and in food products. The reason for this is that all of the *Listeria* phages known in the art at the time of the disclosure in the previous patents were temperate phages, and were therefore not efficient at nor suitable for industrial bacterial eradication purposes. The term "temperate" refers to the fact when a strain of phage injects its DNA into a bacterial target, the phage DNA integrates into the DNA of the host cell, as a "prophage", and can remain integrated therein for considerable periods of time. Since the prophage excises (and initiates replication and lysis) only when the host cell becomes stressed, the ensuing bacterial lysis is unpredictable and not easily controlled, which is why temperate phages do not lend themselves well to industrial applications. Temperate phages are unsuitable for industrial decontamination purposes for other reasons as well, including the fact that they can deliver unwanted and dangerous genes to the bacteria target into which their DNA integrates. In contrast, there is a class of phages that lyse bacterial targets directly, given that they do not have the molecular machinery required to integrate into the bacterial targets. Such phages are referred to as being "virulent" or "lytic" for the bacterial targets. Virulent phages against *Listeria monocytogenes* were discovered recently, by one of the present inventors.

The first of these virulent *Listeria* phages, designated A511, was described in the literature in 1990 (see Loessner et al., Applied and Environmental Microbiology, Jun. 1990, p. 1912-1918, 1990). See also DE 43 26617 C; Loessner et al., Applied and Environmental Microbiology, April 1996, vol. 62, No. 4, p. 1133-1140; and Gaeng et al., Applied and Environmental Microbiology, July 2000, vol. 66. No. 7, p. 2951-2958. The virulent phage according to the present invention belong to the Myovirdae family and have tails which contract towards the virus head. One particularly preferred phage is designated P100 and was deposited at the American Type Culture Collection, 10801 University Blvd., Manassas Va. 20110-2209 on May 23, 2002, 2002, ATCC patent deposit designation number PTA-4383.

The virulent phages described in the present invention can also be used against CFUs (colony forming units) of *Listeria monocytogenes* bacteria that are in biofilms, as opposed to CFUs that are planktonic. The use of temperate *Listeria monocytogenes* phages against *Listeria* biofilms has been described in the literature (see e.g. Roy et. al., Appl. Environ. Microbiol., September, 59(9):2914-7, 1993). Specifically, Roy et. al. used temperate *Listeria* bacteriophages H387, H387-A, and 2671 of the Siphoviridae family. While these temperate phages demonstrated some efficacy in clearing a *Listeria* biofilm, even when used in combination the best they could obtain was a 3.5-3.7 log reduction in counts. Roy et al indicates that such reductions "will have to be improved on to meet the recommended reduction level of 99.999% in a 30-s exposure for a chemical sanitizing agent". As stated above, temperate phages are not predictable or readily controllable in the timing of or efficiency with which they can kill the target bacteria.

In addition to the use of the virulent phages described above, the present inventors have also found that virulent substrains can be derived from a number of temperate phage strains. These virulent substrains can be selected by techniques such as plaque isolation (in which one selects the clearest areas of a plaque, and enriches for the most virulent strains therein by repeated cycles of growing to high titer, plating for new plaques, and picking the clearest areas of the later-generation plaques). Examples of temperate phage strains, from which virulent substrains have been or will be developed, include the temperate strains designated A118, A502, A006, A500, PSA, P35, and related viruses.

The detection of *Listeria* is carried out in a known manner by means of procedures based on the culture of the microorganisms. The procedure described in Int. J. Food Microbiol. 4 (1987), 249-256 takes two weeks. A somewhat more rapid procedure is recommended by the International Dairy Foundation (IDF); however it takes at least 6-8 days. Because of their length, both procedures are unsuitable for a rapid identification. Both procedures are moreover labor-intensive, as for the production of individual colonies nutrient media have to be inoculated several times, and as the isolates then have to be characterized by means of biochemical and serological investigation methods.

A prerequisite for the use of immunological tests is that the antigen is expressed, which is not the case for all proteins at any time. The tests admittedly last only a few hours, but in these procedures a two-day pre-enrichment culture is needed, as the detection limit is $10-1000 \times 10^3$ cells. DNA probes have a detection limit of the same order of magnitude. A prior multiplication of the bacteria is therefore also necessary for these procedures: foodstuff samples or dilutions thereof are streaked out on agar plates, and the inoculated plates are incubated and then investigated in the colony hybridization procedure using a radio-labelled DNA probe. Detection is carried out by autoradiography. This method too is moreover labor and time-consuming.

The polymerase chain reaction (PCR) allows the in vitro replication of nucleic acids; a preculture is in general not necessary in this procedure. The detection limit is $0.5 \times 10^3$ cells. As, however, DNA from dead cells or alternatively isolated DNA is also replicated in this procedure, contamination with dead cells cannot be differentiated from contamination with living cells.

The limitations of these methods indicate the need to provide improved agents and methods for the detection of bacteria of the genus *Listeria*.

EP 0 168 933 (U.S. Pat. No. 4,861,709) discloses a detection procedure for bacteria, e.g., *Escherichia coli*, based on the use of a recombinant bacteriophage. This phage contains the lux gene from *Vibrio fischeri* and thus makes possible the detection of *E. coli* by bioluminescence with a good detection limit ($0.5 \times 10^3$ cells). Using temperate phages, G. J. Sarkis et al. (1995) Molecular Microbiology 15, 1055-1067 describe a detection procedure for mycobacteria. In these detection procedures, only metabolically active bacterial cells are detected; interference due to dead bacterial cells as in the PCR technique does not occur.

Scherer, et al., U.S. Pat. No. 5,824,468, issued on Oct. 20, 1998 describes a detection procedure for bacteria of the genus *Listeria*, where a DNA vector is prepared which includes a genetic system comprising DNA which encodes the expression of one or more detectable proteins, and a DNA vector A511 is used which specifically infects the bacteria of the genus *Listeria* and transfers the genetic system to the bacteria. The detectable proteins are expressed in the bacteria and detection of the detectable proteins indicates the presence of bacteria of the genus *Listeria*.

Phage-encoded lysins or endolysins are highly active enzymes which hydrolyze bacterial cell walls. These phage encoded cell wall lytic enzymes are synthesized late during virus multiplication and mediate the release of progeny virions. Endolysins can be used to lyse *Listeria* cells to recover nucleic acids or cellular protein for detection or differentiation. The endolysin can also be used to treat animals (including humans) which are infected with *Listeria* and to treat surfaces which may be contaminated with *Listeria*. Lysins from *Listeria* phages (A118, A500 and A511) have been cloned and purified (Loessner, et al., Applied and Environmental Microbiology, August 1996, p. 3057-3060).

2. Description of the Related Art

*Listeria monocytogenes* is a bacterial pathogen that contaminates many food products, the list of which includes but is not limited to soft cheeses, patés, ice cream, smoked and cured fish, frozen seafood, salads, and processed meats. When ingested, these bacteria can produce a disease termed listeriosis, characterized by a variety of symptoms and conditions, including diarrhea, abortion, and encephalitis. Collectively, in the industrialized nations, hundreds of deaths occur each year as a result of *Listeria monocytogenes* food contamination.

The food processing industry has not been sufficiently successful in eradicating *Listeria monocytogenes* bacteria from the environment of the processing plants. As a result, even foods that have been pasteurized at temperatures high enough to kill these bacteria nevertheless become contaminated, post-pasteurization. The bacteria gain access to the foodstuffs through one or more routes, including (i) from the raw materials (e.g. raw milk, and/or milk that has been pasteurized at low temperatures); (ii) from the processing machinery (in and on which the bacteria can grow as biofilms that are difficult to eradicate ); and (iii) from airborne bacteria present in the plant environment which can settle onto the surface of the foodstuffs during curing, packaging, and so on.

Despite the numerous methods used in the food industry to control and prevent *L. monocytogenes* contamination, the bacteria gain access to and persist in the environment of food processing plants. Moreover, they survive the very high concentrations of salt that are present in several food-making processes. The resulting contamination of the foodstuffs (including but not limited to cheeses, pates, cold cuts, hot dogs and other processed foods) leads to scores of deaths each year in developed nations, and also to product recalls whose retail worth each year, in the aggregate, is measured in the hundreds of millions of dollars.

The methods currently in use to control *Listeria* in the food industry include: (i) pasteurization of primary ingredients (e.g. milk) and heat treatment of the products, which is often unsuccessful because recontamination frequently occurs and many products cannot undergo a final (listeriocidal) heat treatment; (ii) application of physicochemical agents such as disinfectants, enzymes, antibiotics, etc., which experience has shown do not reduce the bacterial counts sufficiently; and (iii) attempts to break up biofilms mechanically, which leave sufficient residues of bacteria behind that the foodstuffs still become contaminated.

Additional methods must therefore be made available to the food processing industry in order to protect the health of consumers, and to reduce the exposure of numerous companies to the great cost and the loss of good will that result from such contaminations and recalls.

The present inventors have conducted a series of experiments using a strain of *L. monocytogenes* that is prevalent in the processing plant of a particular manufacturer of soft ("spread") cheeses. That bacterial strain proved to be susceptible to phage P100 in vitro. As will be shown in the Examples section, phage P100 proved able to reduce below measurable/detectable limits the *Listeria* bacteria that had been spiked into a cheese-like matrix.

SUMMARY OF THE INVENTION

Virulent phage P100, as well as other virulent phages from the Myoviridae and Siphoviridae families, and virulent mutants of various temperate strains of phage (such as but not limited to phages B054, A118, A502, A006, A500, PSA, P35 and related viruses) are used in the present invention to control *Listeria monocytogenes* bacteria present on (or within) foodstuffs, as well as those *Listeria monocytogenes* bacteria present in the equipment or the general environment of the food processing plants in which the foodstuffs are being processed. These phage can also be used to treat animals infected with *Listeria monocytogenes*.

Virulent phage P100 is used in the present invention to identify *Listeria monocytogenes* bacteria present on (or within) foodstuffs, as well as those *Listeria monocytogenes* bacteria present in the equipment or the general environment of the food processing plants in which the foodstuffs are being processed and in animals infected with *Listeria monocytogenes*. In the present invention, a recombinant DNA vector is prepared using virulent phage P100 which is specific for *Listeria monocytogenes*. The vector includes a genetic system comprising DNA which encodes the expression of one or more detectable proteins which are not a gene product of *Listeria monocytogenes*. The DNA vector infects the bacteria of the genus *Listeria* and transfers the genetic system to the bacteria. The detectable proteins are expressed by the bacteria and the detection of the detectable proteins indicates the presence of bacteria of the genus *Listeria*.

An endolysin derived from P100 is used to reduce the counts of *Listeria monocytogenes* and/or to prevent their growth in the first place, in foods products (including but not limited to the dairy industry) as well as on processing equipment and other sites in food industry facilities, and as a therapeutic agent for treating animals infected with *Listeria monocytogenes*. Endolysins from *Listeria* phages have high substrate specificity and almost exclusively lyse *Listeria* cells.

The present invention is directed to the use of a class of *Listeria monocytogenes* phages which are particularly suitable for bacterial control methods and for the detection of *Listeria monocytogenes*. The phage are preferably from the Myoviridae family and are virulent against *Listeria monocytogenes* strains of serovar 1/2. In addition, the present invention isolates virulent mutants of temperate strains and uses those specific mutants in the control of bacterial contamination of foodstuffs and of food processing plants.

DESCRIPTION OF PREFERRED EMBODIMENTS

By "vector" is meant a nucleic acid molecule that is capable of self-replication when introduced into a suitable host cell. In general, the vectors used as starting materials for the recombinant vectors of the present invention are bacteriophages which are highly specific, and preferably absolutely specific, for infecting bacteria of the genus *Listeria*, and wherein the recombinant vectors retain that specificity. For example, a suitable vector is the *Listeria* bacteriophage P100, which specifically lyses bacteria of the genus *Listeria* (inevitably lytic). It is a myovirus of complex construction. With respect to essential features, the *Listeria* phage P100 differs from many known *Listeria* phages; the differences relate to morphology, host range, protein profiles (electrophoresis in SDS gel, isoelectric focusing, amino acid composition of the main structural proteins, DNA/DNA hybridization).

For detection of the presence of bacteria of the genus *Listeria*, marker genes are employed. These are genes which can be detected upon infection by the vector of a suitable host cell and subsequent culturing of the cells under conditions suitable for expression of the marker genes. It is preferred that the marker genes are those which do not occur in the bacteria of the genus *Listeria*, and which are inserted into the vector, the phage P100, using recombinant techniques. Such genes and their gene products are known in the art; they include bioluminescent proteins such as the lux gene which occurs in variants in various luminescent bacteria, for example of the genus *Vibrio*. The incorporation of the lux gene allows detection by luminescence measurement. An example of the lux gene is gene luxAB from *Vibrio harveyi*. Other suitable proteins include but are not limited to luciferase and fluorescent proteins such as green fluorescent protein.

The detection reaction can take place on a solid surface including but not limited to a test strip. In this embodiment, the vector containing the marker gene could be reversibly immobilized in or downstream from a sample application zone. Alternatively, the vector could be incubated with the sample prior to application on the test strip. Anti-*listeria* antibodies would be irreversibly immobilized downstream from the vector and the sample application zone. If a sample is applied which contains *Listeria*, the vector would infect the *Listeria* and the detectable proteins would be expressed. As the sample moves down the test strip, the *Listeria* would become immobilized by the anti-*listeria* antibodies. The marker proteins would then be detected in the immobilized *Listeria*.

The endolysin of the present invention can be isolated by techniques known in the art including but not limited to lysis, chromatography, filtration, and centrifugation. The endolysin can be isolated from *Listeria* which have been incubated with P100 or the endolysin can be cloned and expressed in a host bacteria (e.g. *E. coli, L. lactis, S. aureus*, and *B. cereus*). The endolysin can be isolated from the host bacteria or the host bacteria containing the endolysin can be directly applied or administered without isolation of the endolysin. For example, a host bacteria which produces the endolysin could be administered to an animal or applied to a surface where the endolysin would be secreted into the food, onto the surface or into the animal's gut. The endolysin can then attack *Listeria* cells present in this environment. One unit of endolysin activity is defined as the amount of endolysin necessary to decrease the optical density at 600 nm by 0.01/min, at pH 8.0 and 25° C. in a volume of 1 ml, when heat-killed, washed cells of *Listeria monocytogenes* are used as a substrate.

The above-referenced endolysin, host bacteria containing the endolysin and/or phage is applied on or into food products, and/or into various physical sites within the food processing plants, by a number of means including, but not limited to, admixing the endolysin, host bacteria containing the endolysin and/or phage into the food products, spraying the endolysin, host bacteria containing the endolysin and/or phage onto the foodstuffs, spraying the endolysin, host bacteria containing the endolysin and/or phage onto the plant equipment, and/or directly applying the endolysin, host bacteria containing the endolysin and/or phage to the plant equipment. Said applications significantly reduce the numbers of *Listeria monocytogenes* bacteria that would otherwise be present.

The phage, endolysin and/or host bacteria containing the endolysin of the present invention can also be used to treat animals, including humans, infected with *Listeria monocytogenes*. Any suitable route of administration can be used to administer the phage including but not limited to: oral, aerosol or other device for delivery to the lungs, nasal spray, intravenous, intramuscular, intraperitoneal, intrathecal, vaginal, rectal, topical, lumbar puncture, intrathecal, and direct application to the brain and/or meninges. Excipients which can be used as a vehicle for the delivery of the phage, endolysin and/or host bacteria containing the endolysin will be apparent to those skilled in the art. For example, the free phage, endolysin and/or host bacteria containing the endolysin could be in lyophilized form and be dissolved just prior to administration by IV injection. The dosage of administration for the phage is contemplated to be in the range of about $10^3$ to about $10^{13}$ pfu/per kg/per day, and preferably about $10^{12}$ pfu/per kg/per day. The dosage of administration for the endolysin is contemplated to be in the range of about 2-2000 ng/per g/per day, and preferably about 20-200 ng/per g/per day. The phage, endolysin and/or host bacteria containing the endolysin are administered until successful elimination of the *Listeria monocytogenes* is achieved or until the amount of *Listeria monocytogenes* is substantially reduced.

The present invention also covers the use of the phages, endolysin and/or host bacteria containing the endolysin, when used in combination with other anti-*Listerial* agents known in the art. Examples of such anti-*Listerial* agents, which are preferentially combined with phages, endolysin and/or host bacteria containing the endolysin, include but are not limited to:

1. Endolysins (Phage Lysins):

The phage, endolysin and/or host bacteria containing the endolysin of the present invention can be combined with listeriolysins which are enzymes which have been shown to selectively control *Listeria* in food and the enviromnnent (DE4326617C1 and EP 95932002.9)

2. Surface Disinfectants:

The phage, endolysin and/or host bacteria containing the endolysin of the present invention can be combined with known surface disinfectants such as (i) preservatives of various kinds, such as but not limited to benzoic acid and BHT; and (ii) various disinfectants with which the phages are compatible, such as but not limited to quaternary ammonium compounds.

3. Antibiotics

The phage, endolysin and/or host bacteria containing the endolysin of the present invention can be used in combination with known antimicrobial agents (including antibiotics and chemotherapeutic agents) including but not limited to vancomycin, nisin, danofloxacin and neomycin.

4. Enzymes

The phage, endolysin and/or host bacteria containing the endolysin of the present invention can be used in combination with enzymes to aid in breaking up biofilms (e.g. biofilms found in food processing equipment). Such enzymes are known in the art and include but are not limited to polysaccharide depolymerase enzymes, and protease.

5. Surfactants

The phage, endolysin and/or host bacteria containing the endolysin of the present invention can be combined with known surfactants when used to treat food processing equipment. The surfactant helps to wet the surface so that the phage are properly distributed over the various surfaces, and to solubilize and remove dirt so that the *Listeria* are accessible to the phage. Suitable surfactants include but are not limited to Tween 80, 20 and 81 and Dobanols.

6. Bacteriophages Specific for Bacterial Contaminants Other than *Listeria monocytogenes*

The phage, endolysin and/or host bacteria containing the endolysin of the present invention can be combined with phage specific for *Listeria monocytogenes* and/or phage specific for other bacteria known to contaminate food processing equipment and food products. Such bacteria include but are not limited to *E. coli*, and bacterial species from the genera *Salmonella*, *Bacillus*, *Staphylococcus*, *Streptococcus*, *Clostridium*, and *Pseudomonas*.

The phage can be applied in a liquid or a powdered form to food products and food processing equipment. If applied as a liquid, the phage are applied at a concentration of $10^3$ to $10^{10}$ PFU (plaque forming units) per mL and preferably at a concentration of $10^6$ to $10^9$ PFU (plaque forming units) per mL. If applied as a dry powder the phage are applied at a concentration of $10^3$ to $10^{10}$ PFU (plaque forming units) per mg and preferably at a concentration of $10^6$ to $10^9$ PFU (plaque forming units) per mg. The phage can be suspended in a suitable carrier prior to application or drying, including but not limited to protein solutions containing BSA, casein, whey protein, soy bean protein, etc and sugar based carriers containing sugars such as mannitol. The phage can be lyophilized or cryopreserved by vitrification and either suspended in a solution prior to application or applied directly as a dry powder.

Suitable amounts of phage for use in the present invention can be obtained by techniques known in the art, including but not limited to a batch technique where a culture of host bacteria is grown and then seeded with phage. After an amount of time suitable to allow maximal phage propagation and bacterial lysis, the culture is further lysed by physical or chemical means and the lysate spun down. The phage containing supernatant can be used as is or further purified using techniques such as ultrafiltration, chromatography and centrifugation.

The endolysin can be applied in a liquid or a powdered form to food products and food processing equipment. The endolysin is applied in a concentration between 2 to 2000 ng endolysin per ml or per gram of carrier, and preferably between 20 to 200 ng endolysin per ml or per gram of carrier.

As used in the present application, the term "dairy product" is intended to include any food product made using milk or milk products, including but not limited to milk, yogurt, ice cream, cheese, butter, and cream.

As used in the present application, the term "meat product" is intended to include any food product which contains animal tissue, including but not limited to beef, pork, and poultry. The term "ready to eat meat product" in intended to include any meat product which does not require cooking prior to consumption, including but not limited to patés, hot dogs, bologna, salami, and cold cuts.

As used in the present application, the term "fish product" is intended to include any food product which contains tissue from an aquatic animal including but not limited to lobster, crab, fresh water and saltwater fish and other seafoods.

As used in the present application, the term "unpasteurized food product" is intended to include any food product which is prepared using unpasteurized primary ingredients and which does not undergo a final (listeriocidal) heat treatment.

As used in the present invention, the term "salad" is intended to include any food product which contains mixtures of vegetables or fruits, and particularly such mixtures as are presented for consumers to choose from in a display commonly referred to as a "salad bar".

EXAMPLE 1

Eradication of *Listeria monocytogenes* in a Liquid Culture:
Step 1. $10^3$ CFUs of *Listeria monocytogenes* are mixed in a liquid culture.
Step 2. $5 \times 10^8$ PFU of phage P100 are mixed into the liquid culture.
Step 3. As a control, the buffer in which phage P100 was suspended is mixed into an aliquot of the liquid culture.
Step 4. Colony counts of the bacteria are performed at various intervals of time.

Figure 1:
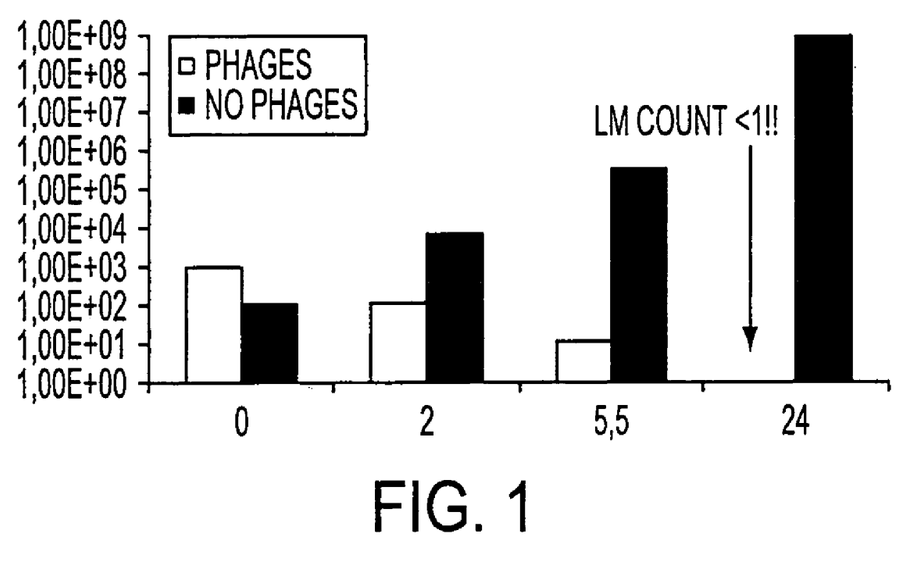
FIG. 1 shows that when *Listeria monocytogenes* is inoculated at $10^3$ CFU per ml of liquid culture and phages added at a concentration of $5 \times 10^8$ PFU per ml—virtually complete eradication of the *Listeria* bacteria occurs.

Results are shown in FIG. 1.

EXAMPLE 2

A challenge experiment was done using a strain of anti-*Listeria monocytogenes* phage known as P100, in a cheese model on lab scale. This experiment incorporated technical flora to achieve the surface-ripening qualities (taste, texture, etc.) characteristic of an established commercial cheese-making process. The strain of *Listeria monocytogenes* ("Lm") known as strain C that was used in this experiment is a common contaminant of a certain cheese-making plant.

Materials and Methods

Challenge Experiment on Cheese
The experiment was carried out on cheese taken directly from the brine (unadjusted pH).
Lm strain C, technical flora, and phage P100 were applied on the cheese at t=0 by plating 210 μL or 1 mL of incubation mix on 64 cm² cheese surface. t=0 is the same as "CMD+1" (Cheese Making Day+1). Cheeses treated with 1 mL solution were subsequently dried in a laminar flow cabinet to dry the surface. The incubation mix consisted of:
110 g/L NaCl
Technical flora:
*Debaryomyces hansenii* NIZO F937 and NIZO F1200 (yeasts) at $10^8$ CFU/mL
*Brevibacterium linens* NIZO B1204 (a bacterium typical for red smear cheese) at $10^8$ CFU/mL
LmC corresponding to a concentration of 7 cfu/cm² (diluted in pfz from an exponential growing culture)
Phage P100 (in MPOS buffer) at a concentration corresponding to $1 \times 10^7$ pfu/cm² or $5 \times 10^5$ PFU/cm²
See Table 1 for exact treatment combinations
The cheeses were incubated at 14° C. and 98%-99% relative humidity
The cheeses were treated daily with 210 μL or 1000 μL washing solution that contains P100, at CMD+6, CMD+10, and CMD+13 and 1 mL/70 cm² (treatment combination 4 and 5)
The washing solution contained:
110 g/L NaCl
*Brevibacterium linens* NIZO B1204 at $10^8$ CFU/mL
Phage P100 (in MOPS buffer) at a concentration corresponding to $1 \; 10^7$ PFU/cm² or $5 \; 10^5$ PFU/cm²
Cheeses were packed using parchment paper, a material that is used to pack Munster cheese, at CMD+16. (CMD+16 is packaging day (PD))
Cheeses were stored at 6° C. until PD+63
LmC counts were analyzed at the time points indicated in Table 1. Analysis was done before treatment with phage.
Quantitatively: samples of 70 cm² were cut out of the cheese and analyzed on selective media.
Qualitatively at CMD+1 and CMD+37 by enrichment procedure.
Qualitative/Quantitative analysis will depend also on the level of outgrowth of *Listeria* on the cheeses. If cell counts are $>10^2$, no enrichments were done. If cell counts were lower, enrichments were done also before packaging.
Furthermore analysis of pH and technical flora.
In one cheese at CMD+6, phage titers were determined before and after application of phage.

Results

The ripening of the cheese was good, since yeast and *Brevibacterium* grew out well on the cheese and the cheese surface was de-acidified.

Figure 2:
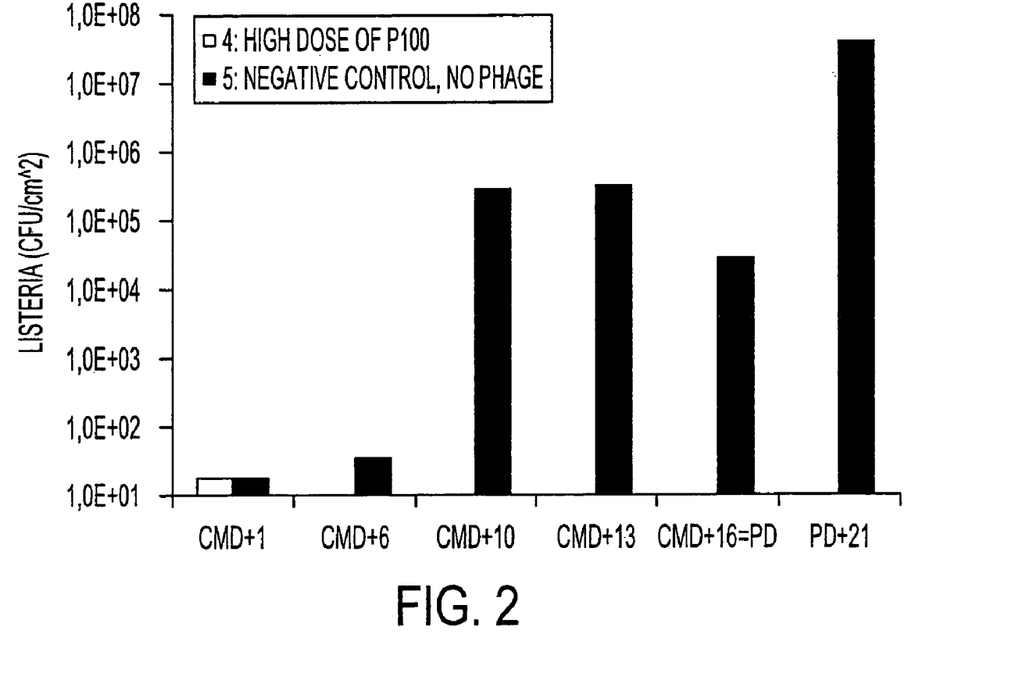
FIG. 2 shows that applying phage P100 to the surface of a surface-ripened cheese completely prevented outgrowth of *Listeria monocytogenes* that had been spiked into the starter culture.

*Listeria monocytogenes* C grew well on the cheese surface in this model, to levels of $10^5$-$10^7$ CFU/cm² in the negative controls (negative control: no phage applied) (FIG. 2).

As seen in FIG. 2, phage P100 completely inhibited growth of LmC. No *Listeria* was detected using the quantitative plate counting method, or on enrichment. The detection limit using the enrichment procedure is in the order of magnitude of one *Listeria* per 60 cm². This indicates that phage P100 not only inhibited growth but actually reduced *Listeria* titers. As shown in FIG. 2 applying phage P100 to the surface of a surface-ripened cheese completely prevented outgrowth of *Listeria monocytogenes* that had been spiked into the starter culture.

Key: CMD=Cheese-making day
PD=Packaging day

Figure 3:
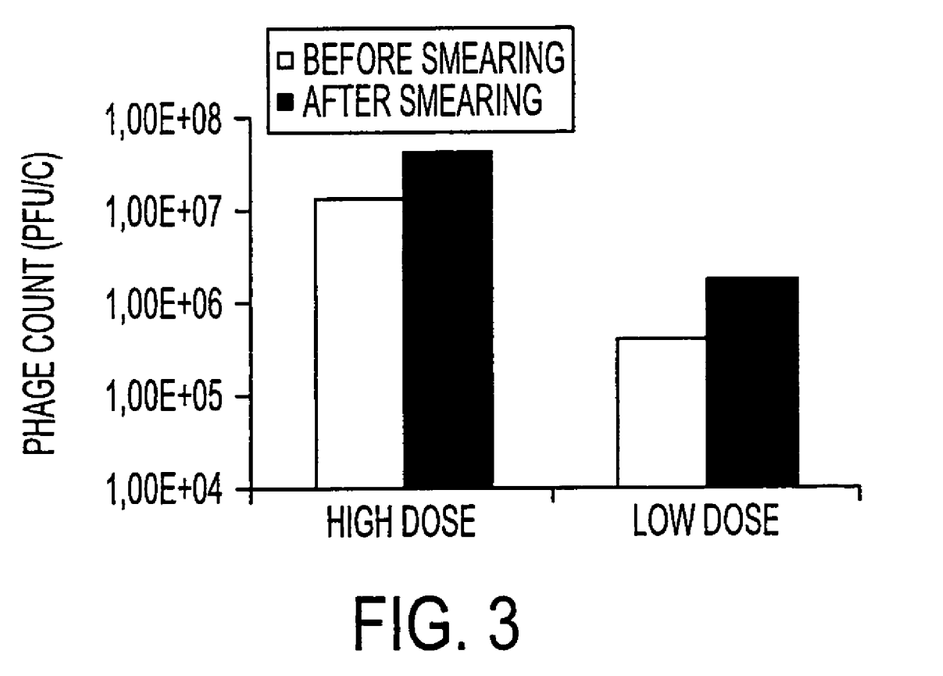
FIG. 3 shows phage titers on cheese (PFU/cm$^2$).

In order to determine if phages can survive on the cheese surface, in another arm of the experiment (in which a high or a low dose of phage was applied to the cheese surface), phage titers were determined at CMD+6, before as well as after application of phage. In all samples, phages had been applied at CMD+1, CMD+2, CMD+3, and CMD+4. Therefore, in the samples taken before the application of phage (at CMD+6), phages had been present on the cheese for at least 48 hours. Active phages were recovered from the cheese surface at both doses (FIG. 3). The phage titers of the samples taken before application of phage at CMD+6 were lower than the samples after application of phage. The increase in phage titer corresponded well with the expected increase based on the dose added (i.e., either $1 \times 10^7$ pfu/cm² or $5 \times 10^5$ PFU/cm²). The results show that phage P100 remains active on the cheese surface for at least several days.

EXAMPLE 3

Assay, Overexpression and Purification of Endolysins from *E. coli* JM109(pHPLxxx) Plate Assay
1. Prepare *Listeria monocytogenes* assay strain for activity testing: grow 1000 ml overnight-culture in tryptose broth or trypticase soy broth, centrifuge, wash cells once with SM Buffer, pH 8.0 (see Sambrook et al., 1989), (or PBS), and resuspend in 20 ml SM Buffer (or PBS) (approx. 50-fold concentration).
2. Store in 1 ml amounts at −20° C. or at −80° C.
3. Streak or plate *E. coli* JM109(pHPLxxx) on LB-agar (containing 100 μg/ml ampicillin), and incubate overnight.

4. When colonies are of sufficient size, prepare replica plate (with NC-filters) on LB-Amp plates supplemented with 1 mM IPTG. Incubate for 5-7 hours until small colonies are visible.
5. Expose surface of plate (upside down) to filter paper saturated with chloroform, for 5 min.
6. Quickly overlay the colonies with 3-4 ml of molten soft agar (0.4%, in SM Buffer, approx. 45° C.), supplemented with 0.5 ml of a 50-fold concentrated *L. monocytogenes* culture (overlay should be thin, even, and quite turbid).
7. Incubate at RT for 60 min (up to overnight), until clear lysis zones around colonies are visible. This can take any time, from 5 minutes to 5 hours. (this is an important assay; it must work. Otherwise there might be a problem with the strain, or the activity testing procedure.)

Production

8. Prepare overnight culture of JM109(pHPLxxx) in LB broth with 100 µg/ml Amp @ 30-35° C. incubation.
9. In the morning, inoculate 250 ml prewarmed broth with 10 ml O/N culture, grow to OD600 of 0.5-0.6.
10. Induction with 1 mM IPTG, incubate for further 3-4 h until the growth rate begins to cease.
11. Harvest cells by centrifugation, resuspend pellet(s) in 5 ml per 250 ml culture PBS (pH 8.0) 0.05% Tween20 or, if downstream Ni—NTA purification is required, Buffer A (see below). Freeze cells at –20° C.
12. Thaw cells. Prepare cell extracts by French-Press; centrifugation (>30000×g, 30 min); and filtration of supernatant (0.2 µm filter, preferably made from PES). Store the enzyme containing extract on ice (a few hours), or at –20° C. (note: sonication can also be used, but yields obtained by French-Press are generally much better).

Photometric Activity Assay (OD 600)

13. Use freshly grown, mid-to-end-of-log-phase-cells, or the previously frozen *L. monocytogenes* cells from Step 1 (above). Resuspend in PBS Buffer, pH 8.0, 0.05% Triton X100 (adjust OD to approx. 1.0-1.5). Use half-micro plastic cuvettes (1 ml); add 900 µl cells, prewarm to at least RT but preferably 30-37° C., and add 50-100 ml enzyme. Turbidity should drop to 0.5 or below within 5 minutes or less.
This crude extract can be used for lysis of *Listeria* cells and release of chromosomal DNA, Plasmids, proteins and enzymes. However, it contains high amounts of *E. coli* proteins, nucleic acid (DNA, RNA) fragments, ATP, and contaminating pHPL vector. If this is not desirable, purify the enzymes by IMAC (see below).

Purification

14. Fractionation of crude extracts with Ni—NTA-Resin. The procedure outlined in steps 8-11 is for liquid chromatography (FPLC or similar, see step 15), and is highly recommended. However, for small scale purification, it can also be performed in a more simple batch-type procedure:. Use approximately 3 ml resin (NiNTA Agarose) per 250 ml initial culture volume. After exposure of resin to proteins, carry out wash steps (in batches) by low speed centrifugation (less than 500×g). After the last wash, harvest resin and aliquot in portions of 1-2 ml into small disposable plastic columns (available from BioRad and others); place into 15 ml conical or round bottom tubes. Add elution buffer (approx 1 ml) (100% B), let stand for 5 minutes, spin and collect liquid. Repeat elution 1-2 times. Continue with step 19.
15. FPLC Purification: Prepare sufficient amounts of Buffer A (50 mM phosphate buffer, pH 8.0, 500 Mm NaCl, 5 mM imidazole) and Buffer B (same as A, but 250 mM imidazole). Use imidazole gradient with Buffers A and B. Load extract (up to 40 ml=extract from 2 liters (8×250 ml) of culture) on Ni—NTA column (25 ml volume), Use a low flow rate (0.75 to 1.0 ml/min). If necessary, regenerate Ni—NTA resin (Ni—NTA Superflow) before purification of each individual enzyme by the procedure outlined in the handbook from Qiagen. A new or regenerated column can be used for at least 5 runs.
16. Wash with at 5 column volumes of 100% Buffer A (flow rate 2 to 3 ml/min)
17. Wash with 3-5 column volumes of 12% Buffer B (total conc. approx. 35 mM Imidazole), until the baseline reading (@ 280 nm) is stable. This step will remove most contaminating proteins (be aware that Imidazole itself increases the reading at 280 nm !).
18. Elute enzyme fraction with 250 mM Imidazole (100% buffer B). It is best to collect the peak manually (regarding the right shoulder of the peak, stop early—don't be fooled by the higher absorption of imidazole itself). Store on ice. Do not freeze the freshly eluted fractions, the enzymes have a tendency to cold precipitate in the presence of high salt and imidazole!
19. Check all eluted fractions by photometric activity assay (see above).
20. Concentration and buffer-exchange (removal of imidazole and high salt) of active fractions with centrifuge filter units (PES membrane, Mr cut-off 10 kDa). Pre-treat membrane with Lysis Buffer (PBS, pH 8.0, 0.05% Triton X100, 0.05% Tween20). Wash twice with 5 ml lysis buffer. In case membrane gets plugged with protein, transfer to new filter unit. Filter—sterilize using a 0.2 µm syringe filter (use PES membrane—Cellulose will retain much of the enzymes!). Alternatively, buffer exchange can be performed by dialysis of concentrated protein solution (PBS or Tris buffers, 0.05% Tween20). We found that HPL118 (but not HPL511 or HPL500) has a tendency to aggregate during prolonged dialysis.
21. Check fractions by SDS-PAGE, estimate protein purity (Should be more than 90% pure), and protein concentration (typically in the range of 2-4 mg/ml). If the preparation is not of sufficient purity, try to wash column (Step 10) with 15% Buffer B, and elute HPL proteins with 150 mM Imidazole (60% Buffer B), or 200 mM Imidazole (80% Buffer B). One can also "reload" the entire initial protein prep (dilute at least 10-fold before reloading, or dialyse to remove imidazole) onto the column, and perform a 2nd step purification using altered conditions, such as a pH gradient. Gel-filtration also further increases protein purity. However, this is certainly not needed for all standard applications.
22. Adjust concentrated enzyme solution to a final content of 30-50% Glycerol, aliquot into 50-500 µl portions, store at –25° C. Under these conditions, enzymes are stable for several months. Freezing at –80° C. sometimes resulted in loss of activity.

DISCUSSION AND CONCLUSION

When *Listeria monocytogenes* bacteria were spiked onto the surface of a surface-ripened cheese along with the starter culture, applications of a sufficient dosage of Phage P100 to the surface completely eradicated the bacteria, as confirmed by enrichment studies (detection limit using enrichment: one *Listeria* CFU per 60 $cm^2$ of cheese surface). In all cheeses treated with phage (high or low concentration, one application or multiple), *Listeria* titers after treatment with P100 were lower than in the controls. *Listeria* emerged only when phages were applied only once (instead of on multiple time points) or at low concentration. Phages can remain active on cheese for several days.

We claim:

1. A method for controlling *Listeria* contamination of a food product, food processing equipment, or a food storage container, comprising applying lytic phage P100, ATCC patent Deposit Accession No. PTA-4383, to said food product, equipment or container in an amount sufficient to reduce the amount of *Listeria*, thereby controlling said *Listeria* contamination.

2. The method according to claim 1, wherein said P100 is applied in combination with phage A511, ATCC Patent Deposit Accession No. PTA-4608.

3. The method according to claim 1, wherein said lytic P100 phage is applied in combination with at least one additional agent selected from the group consisting of listeriolysin, a surface disinfectant, an antibiotic, a surfactant, an enzyme, and a phage that lyses a contaminating bacteria other than *Listeria monocytogenes*.

4. The method according to claim 1, wherein said food product is a dairy product.

5. The method according to claim 1, wherein said food product is an unpasteurized food product.

6. The method according to claim 1, wherein said food product is a meat product.

7. The method according to claim 6, wherein said meat product is a ready to eat meat product.

8. The method according to claim 1, wherein said food product is a fish product.

9. The method according to claim 1, wherein said container is a salad bar and said food product is salad.

10. The method according to claim 1, wherein said food processing equipment is selected from the group consisting of
   (i) tube through which milk is being pumped,
   (ii) a high-salt content tank for processing cheese,
   (iii) a container from which cultures are applied to a surface of a cheese,
   (iv) a set of shelves on which a product is dried and cured, and
   (v) a floor drain.

11. The method according to claim 1, wherein said lytic P100 phage is applied by mixing the phage with a liquid or semi-solid food product.

12. The method according to claim 1, wherein said lytic P100 phage is suspended in a liquid and sprayed onto a surface of said food product, equipment or container.

13. The method according to claim 12 wherein said lytic P100 phage are sprayed onto said food processing equipment surface in combination with an agent selected from the group consisting of listeriolysin, a surface disinfectant, an antibiotic, a surfactant, an enzyme, and a phage that lyses contaminating bacteria other than *Listeria monocytogenes*.

14. The method according to claim 1, wherein said lytic P100 phage is lyophilized or cryopreserved by vitrification and applied in a dry form to said food product, equipment or container.

15. A composition comprising an isolated P100 phage, ATCC Patent Deposit Accession Number PTA-4383 in a carrier.

16. The composition according to claim 15, further comprising, in said carrier, an isolated A511 phage, ATCC Patent Deposit Accession Number PTA-4608.

17. The composition according to claim 15, farther comprising an agent selected from the group consisting of listeriolysin, a surface disinfectant, an antibiotic, a surfactant, an enzyme, and a phage that lyses contaminating bacteria other than *Listeria monocytogenes*.

18. The composition according to claim 15, wherein said carrier is a pharmaceutically acceptable carrier.

19. An isolated P100 phage as deposited at the American Type Culture Collection, ATCC Patent Deposit Accession Number PTA-4383.

\* \* \* \* \*

UNITED STATES PATENT AND TRADEMARK OFFICE
CERTIFICATE OF CORRECTION

| | | |
|---|---|---|
| PATENT NO. | : 7,438,901 B2 | Page 1 of 1 |
| APPLICATION NO. | : 10/516507 | |
| DATED | : October 21, 2008 | |
| INVENTOR(S) | : Loessner et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 699 days.

Signed and Sealed this
Twenty-second Day of November, 2011

David J. Kappos
*Director of the United States Patent and Trademark Office*